(12) United States Patent
Stannard

(10) Patent No.: US 7,157,502 B2
(45) Date of Patent: Jan. 2, 2007

(54) POLYMERIZABLE DENTAL BARRIER MATERIAL

(75) Inventor: Jan G Stannard, Hanover, MA (US)

(73) Assignee: Pulpdent Corporation, Watertown, MA (US)

( * ) Notice: Subject to any disclaimer, the term of this patent is extended or adjusted under 35 U.S.C. 154(b) by 434 days.

(21) Appl. No.: 10/368,934

(22) Filed: Feb. 19, 2003

(65) Prior Publication Data

US 2004/0161724 A1  Aug. 19, 2004

(51) Int. Cl.
*A61K 6/083* (2006.01)
*A61C 5/00* (2006.01)
*C08F 2/46* (2006.01)

(52) U.S. Cl. ............... 523/105; 523/111; 523/120; 522/33; 522/47; 522/96; 433/228.1

(58) Field of Classification Search ........... 523/105, 523/111, 120; 522/33, 47, 96
See application file for complete search history.

(56) References Cited

U.S. PATENT DOCUMENTS

| | | | | |
|---|---|---|---|---|
| 3,769,336 A | * | 10/1973 | Lee, Jr. et al. | 560/224 |
| 4,813,875 A | * | 3/1989 | Hare | 433/214 |
| 4,952,241 A | * | 8/1990 | Reiners et al. | 106/35 |
| 5,177,120 A | * | 1/1993 | Hare et al. | 523/109 |
| 5,880,172 A | * | 3/1999 | Rajaiah et al. | 523/120 |
| 6,048,202 A | | 4/2000 | Jensen et al. | 433/136 |
| 6,086,370 A | | 7/2000 | Jensen et al. | 433/136 |
| 6,335,385 B1 | * | 1/2002 | Gorlich et al. | 264/17 |
| 6,800,671 B1 | | 10/2004 | Montgomery et al. | 523/105 |
| 6,936,642 B1 | * | 8/2005 | Lehmann et al. | 523/115 |
| 2002/0082315 A1 | * | 6/2002 | Moszner et al. | 523/106 |
| 2005/0084224 A1 | * | 4/2005 | Greer et al. | 385/128 |

\* cited by examiner

*Primary Examiner*—Tae H. Yoon
(74) *Attorney, Agent, or Firm*—Cesari and McKenna, LLP; John L. Capone, Esq.

(57) ABSTRACT

This invention relates to a polymerizable dental barrier material and method of making same including at least one high molecular weight polymer with reactive end groups having a concentration ranging from about 50 to about 99 percent by weight and a polymerization system.

35 Claims, No Drawings

POLYMERIZABLE DENTAL BARRIER MATERIAL

FIELD OF THE INVENTION

This invention relates to polymerizable dental barrier materials and, more particularly, polymerizable dental barrier materials for isolating dental tissues during dental procedures.

BACKGROUND OF THE INVENTION

In the course of dental treatment, it is often necessary or desirable to isolate oral tissue from a treatment area. This isolation may protect the isolated oral tissue from materials, such as caustic, acidic or abrasive materials, used during treatment. The isolation may also serve to maintain improved control over the treatment area by the reduction of oral fluids and to ensure a dry field, free of contaminates or other tissue.

In the past, cotton rolls, absorbent materials, or rubber dams and frameworks have been used to isolate dental tissues. These materials have been limited by their ability to achieve complete isolation of tissue directly adjacent to a treatment area. For example, cotton rolls or other absorbent material will absorb moisture or water rendering them of temporary benefit. A rubber dam framework does not work well in isolating the tissue nearest a treatment site and can be difficult to apply. A rubber dam is also not effective in isolating newly erupted teeth where clamping of a framework is not possible due to limited exposed hard tissue.

An alternative method to isolate dental tissues is to use polymerizable isolation barrier materials. In general, these materials are formulated with low molecular weight, difunctional monomers which generate hard, crosslinked structures when polymerized. Typically, monomers have molecular weights ranging from about 100 to 600. Currently available polymerizable isolation barrier materials are typically comprised of Bis-GMA (Bis phenol A glycidal methacrylate) and TEGDMA (tri-ethylene, glycol dimethacrylate) having low molecular weights of 512 and 286, respectively. When polymerized, these compounds or monomers react together hundreds or thousands of times before a completely set material is obtained. Fully reacted materials may contain polymers having molecular weights of one million or more.

The problems with the current polymerizable tissue barrier materials have been noted, e.g., in U.S. Pat. No. 6,086,370, and include, but are not limited to, the heat of polymerization causing a painful response from a patient, the cured material being too rigid making it difficult to remove from undercuts or situations where the materials can interlock within tooth structures, the material prior to curing being of low viscosity causing the material to run or displace from its original position, and the material not adhering well to tissue making accurate placement of these materials difficult.

Previous attempts have been made to alleviate these problems. In U.S. Pat. No. 6,086,370, reflective substances were incorporated within the barrier material in an attempt to reduce the amount of light absorbed during curing and thus change the rate of polymerization and/or heat of polymerization. Tissue adherence substances, such as gums, cellulose, or polyols were also incorporated within the barrier material in order to improve tissue adherence. However, the amount of heat generated during curing and the tissue adherence may still be improved.

Significant amounts of filler material are often added to render the barrier materials more viscous or less flowable. However, high amounts of fillers impart undesirable rigidity to these materials. A rigid, non-pliable material is difficult to remove from certain areas, such as an undercut, and may pinch adjacent tissues, causing patient discomfort. The removal of rigid, non-flexible material may necessitate the use of dental cutting instruments, which can damage adjacent tooth structures. A flexible material that is easy to bend may be easily removed from between teeth or from an undercut. Such a pliable material elongates or deforms to allow easy removal.

Some tissue barrier materials are supplied in colors, such as blue or green, to provide good contrast to oral tissue colors such as white (tooth) or red (gingival). However, such colored formulations tend to increase the heat generated in the material during curing due to light absorption. A limitation of white, reflective materials is the lack of contrast with tooth-like colors. This limitation may be important where the tissue barrier material is used in bleaching or tooth whitening. A color contrasting the original or final tooth shade is beneficial to identify the tooth color and to distinguish the tissue barrier material.

Due to the heat generated during the curing of barrier materials, dentists are often instructed to limit the patient discomfort by curing the material for only 1–2 seconds at a time. Typically, these materials require 10–20 seconds of intense light exposure to one applied area by an appropriate light curing source to cure completely. A material with a lower heat of polymerization enables the barrier material to be continuously cured and provides a quicker, more efficient process.

SUMMARY OF THE INVENTION

In general, in one aspect, the invention features a polymerizable dental barrier material including at least one high molecular weight polymer with reactive end groups having a concentration ranging from about 50% to about 99% by weight and a polymerization system.

In general, in another aspect, the invention features a polymerizable dental barrier material including at least one high molecular weight polymer with reactive end groups having a concentration ranging from about 50% to about 99% by weight, a monomer having a concentration ranging from greater than 0% to about 10% by weight and a polymerization system.

In general, in another aspect, the invention features a method for making a polymerizable dental barrier material. At least one high molecular weight polymer with reactive end groups having a concentration ranging from about 50% to about 99% by weight is provided, and a polymerization system is added.

An advantage of the present invention is that the barrier material has a lower heat of polymerization which reduces or eliminates the painful response in a patient due to the heat generated during curing. An additional advantage of the present invention is that the lower heat of polymerization allows the addition of opacifiers or pigments without raising the heat generated during curing to an unacceptable level. Additionally, one embodiment of the invention provides a barrier material which uses a reduced amount of setting chemistry thereby lowering the heat generated during curing.

The details of one or more embodiments of the invention are set forth in the description below. Other features, objects, and advantages of the invention will be apparent from the description, and from the claims.

BRIEF DESCRIPTION OF THE INVENTION

The present invention relates to polymerizable dental barrier materials and methods of making such materials in which a tough, pliable, dental barrier material with a lower heat of polymerization is produced. The polymerizable dental barrier material includes at least one high molecular weight polymer with reactive end groups having a concentration ranging from about 50% to about 99% by weight and a polymerization system.

The dental barrier material may additionally contain other adjuncts to impart convenient handling characteristics and satisfy setting or curing requirements and other suitable qualities useful in the field of dentistry. For instance, the barrier material may contain a monomer to increase the toughness and/or reduce the viscosity of the material, a plasticizer to reduce the heat generated during curing, reduce the viscosity of the material, and soften the cured material, a filler material to increase the viscosity of the material and rigidity of the cured material and opacifiers or pigments to provide a desirable appearance to the cured material.

The present invention utilizes a mixture of high molecular weight polymers with reactive end groups, that when further reacted produce very little exothermic reaction. High molecular weight polymers of the present invention have molecular weights ranging from about 5,000 to about 50,000. The appropriate selection of a reactive polymer may result in a cured, final product that is soft and pliable. For example, linear aliphatic polymers may have percent elongation at failure from 20–50%. Current polymerizable barrier materials using monomers are stiff after curing and elongate only 2–5% before failure. The molecular weight and structure of the reactive polymer should be sufficient so that a flexible material results after curing. For example, the overall reaction may be reduced considerably by selecting a polymer already having a molecular weight greater than about 5,000. In part, the number of reactions and the total available reacting units are responsible for the reduced amount of heat generated during curing or polymerization. Furthermore, the heat of reaction may be lowered by reducing the amount of setting chemistry used, since less absorbed energy is needed in the reaction to achieve the final, cured product. Polymers with reactive end groups of the present invention may include reactive silicones, acrylics, urethanes, polyethers, polysulfides, or combinations of many different polymers that can be prepared with terminal polymerizable groups. Polymers of the present invention are provided in a concentration ranging from about 50% to about 99% by weight, and preferably from about 60% to about 95% by weight.

The polymerization system of the present invention typically includes compounds, such as initiators and accelerators, which enable polymerization of the barrier material. The polymerization system of the present invention is preferably provided in a concentration ranging from about 0.15% to about 3.5%. The polymerization system includes either single compounds or compounds working in conjunction to initiate polymerization either by auto polymerization or by light curing, such as using a dental curing lamp.

For example, a self polymerization initiator may be used to create a two-part system that cures when the components are mixed together, and a light absorber may be used to initiate curing in a single system when the material is exposed to a sufficient amount of light. Suitable initiators of the self polymerization type include compounds such as benzoyl peroxide, cumene hydro peroxide, lauryl peroxide and a variety of other similar compounds known to those skilled in the art. Suitable light absorbers include camphorquinone, diphenyl (2,4,6 trimethylbenzoyl) phosphine oxide, benzil, benzoin, or other suitable compounds capable of absorbing transmitted light to initiate polymerization as well known to those skilled in the art.

Accelerators to accompany polymerization initiators include compounds, such as amines, sulfonates or their derivatives typically selected from N,N dimethyl-p-toluidine, hydroxy ethyl-p-toluidine, ethyl-4-dimethyl amino benzoate, and p-toluene sulfinic acid, as well as other suitable compounds well known to those skilled in the art.

The addition of an appropriate low molecular weight monomer as a minor component may impart some toughness to the final, cured product. However, the monomer should not be present in a sufficient amount to increase the heat generated during curing. Since the monomer or monomers have low molecular weight, the monomers may reduce the viscosity, making the barrier material more easily dispensed. Monomers of the present invention may include di-or trifunctional monomers, which contain 2, 3 or more reducible double bonds within the monomer. Examples of such monomers include trimethyol propane trimethacrylate, pentaerythritol trimethacrylate, pentaerythritol tetramethacrylate, dipentaerythritol penta acrylate, and similar compounds well known to those skilled in the art. Monomers of the present invention are provided in a concentration ranging from 0% to about 10% by weight, and preferably from 0% to about 5% by weight.

The addition of appropriate plasticizers can further reduce the amount of heat generated during the setting of the product as well as render the final material pliable and soft. Suitable plasticizer materials of the present invention include compounds such as dimethyl phthalate, Bis(2-butoxy ethyl) phthalate, Bis(2-butoxyethyl) adipate, tri(ethylene glycol) bis (2-ethyl hexanoate), tri(ethylene glycol) diacetate, as well as generally recognized plasticizers well known to those skilled in the art. Plasticizers of the present invention are provided in a concentration ranging from 0% to about 45% by weight, and preferably from 0% to about 30% by weight.

The addition of appropriate filler materials may produce a material with desired physical properties. Typically, filler materials are particles used to impart strength to the barrier material or vary the viscosity of the barrier material. The filler may contain particles of varying sizes. For example, the filler may include micron-sized or submicron-sized particles of silica ($SiO_2$). Micron-sized particles typically provide density, while submicron-sized particles typically act as a thickening and suspending agent. Suitable filler materials of the present invention include silica, talc, titanium dioxide, bentonite, potassium aluminum silicate, quartz, barium aluminum silicate glass, and other non-reactive compounds well known to those skilled in the art. Filler materials of the present invention are provided in a concentration ranging from 0% to about 50% by weight, and preferably from 0% to about 25% by weight.

The addition of appropriate opacifiers and pigments may produce a material with a variety of translucent to opaque effects or colors as desired. Suitable opacifiers of the present invention include compounds such as titanium dioxide, zinc oxide, magnesium oxide or other oxides known to be only cosmetic in their use. Appropriate pigments of the present invention may be selected from iron oxides both natural and synthetic, FD&C approved pigments and lakes thereof in addition to many other generally recognized colorants for food, drug, cosmetic or dental use, as well known to those skilled in the art.

The polymerizable barrier material of the present invention may be made in a variety of forms depending upon the selected application. For example, the polymerizable barrier material may be a paste or gel, e.g., easily dispensed through a conventional dental syringe or applicator tip of approximately 20-gauge size or may be a formable solid, e.g., pressed or rolled into place. In one embodiment of the present invention, the material possesses sufficient viscosity or resistance to flow so that the material remains in place and does not run after being dispensed. The material is easily and rapidly cured using a conventional dental light curing unit. Upon curing, the material does not generate sufficient heat to cause a burning or painful response in a patient. The material possesses sufficient tissue adherence to soft or hard dental tissues in a moist or desiccated condition and remains in place for several hours without being disrupted by incidental contact. The color of the barrier material may be altered to provide contrast to and distinguish it from the tooth color. The material may be soft enough to easily trim with scissors or a scalpel if excess material needs to be removed. After curing, the material is easily removed, usually in a single piece, without causing patient discomfort and without having problems with undercuts or surfaces where binding typically occurs.

To further illustrate the present invention, the following examples are provided, but the present invention is not to be construed as being limited thereto. In the examples, the temperature rise was measured as the difference between the initial temperature of the sample and the maximum temperature obtained by the sample during curing. Samples were prepared by forming the material into a cylinder 3.5 mm diameter by 4.0 mm high. The samples were cured in a plastic mold with a thermocouple temperature probe placed in an opening at the base of the mold. Over the top of the material was placed a glass microscope slide. The starting temperature was 70° F.±1° F. The material was cured using a Demetron Optilux 150 dental curing light, continuously operated. The amount of material used in the samples is thicker than clinically applied, while the width is less than normal. In clinical use, the thickness is approximately 1–2 mm, and the width is approximately ¼ inch to several inches.

To test the flow characteristics both during and after application, a bead of material was extruded through a 20 gauge applicator tip to a length of about one inch on a mixing pad. The mixing pad was then turned to a vertical position with the line in a horizontal orientation. A material of sufficient viscosity is easily extruded through an applicator tip of approximately this size, but does not run down the surface of the pad when this test is performed.

Other properties of importance were assessed by simple manipulation or testing. For example, the rigidity or pliable nature of the materials was assessed by attempting to bend a cured sample by placing a one-inch segment of the material between the thumb and forefinger. Dental barrier materials of the present invention were easily bent back upon themselves such that the ends were 30° apart from one another without breaking. Currently available dental barrier materials cannot be bent using finger pressure or snap in a brittle failure when a great enough force is applied. Placing a sample of the material on a moistened fingertip was used to assess the temperature rise during curing or the adhesion of the material after curing, qualitatively. Care should be taken when performing this test as sufficient heat is generated by some commercial materials as well as by some curing lights, to be painful.

Additional tests such as ability to cut the material with scissors, ease of spreading the material, spraying an adhered material with water to assess tissue adhesion, and ease of removal of the material after placement were conducted to further demonstrate the desired and improved properties of the dental barrier material of the present invention. These tests show the desired behavior of the material for one embodiment of the present invention, but the material may exhibit other behavior when used in different applications.

For all examples herein, the percentages given are by weight.

EXAMPLES

Example 1

Example 1 was an evaluation of LumaBlock, commercially available from LumaLite, Inc. (Spring Valley, Calif.). Prior to curing, the material ran easily over applied tissue or when dispensed on a mixing pad. Table 1 shows the temperature rise value measured, 6.4±1.4° F. Curing of the material upon the finger or in an intra-oral application caused a significant heat sensation, which was painful for some individuals. After curing, the material was very hard and rigid. LumaBlock has an off-white appearance, both before and after curing.

Example 2

Example 2 was an evaluation of Opal Dam, commercially available from Ultradent Products, Inc. (South Jordan, Utah). This material contains sparkles and has an off-white color both before and after curing. After curing, the material was very rigid and was not easily manipulated from around tissue undercuts. Table 1 shows the temperature rise value measured, 6.4±1.5° F. This material caused a burning sensation when cured upon the finger and created a painful reaction when cured intra-orally.

Example 3

A polymerizable dental barrier material of the present invention containing 87.77% of a high molecular weight aliphatic urethane acrylate polymer having reactive end groups was prepared. Table 2 shows the composition of the material. The polymer had a molecular weight of 20,000 and viscosity of approximately 35,000 c.p.s. The polymer was compounded with a small amount of titanium dioxide, silica, camphorquinone and a suitable amine. The resulting material was easily extruded through a 20 gauge needle applicator tip. A bead of the material did not run when placed on the mixing pad and turned to a vertical position. Table 1 shows the temperature rise value measured, 5.5±0.5° F.

When placed on tissue and cured, the material adhered to both moist and dry tissue. When placed on the gingiva, intra-orally, the material adhered well to the tissue and no heat sensation was detected upon continuous, direct curing. The material did not dislodge when water spray from a dental handpiece was applied to the material. The material was easily removed from the tissue when desired and often in a single piece. Since the material was pliable, the removal process did not pinch adjacent soft tissue.

The color of the material, both before and after curing, was off-white. The appearance of the material was very similar to the material in Example 1, however the mechanical properties, behavior and performance of the two materials were quite different.

Example 4

A polymerizable dental barrier material of the present invention containing 78.09% of a high molecular weight aliphatic urethane acrylate polymer with reactive end groups was prepared. The molecular weight of the urethane acrylate was approximately 25,000 and the viscosity was approximately 45,000 c.p.s. Table 2 shows the composition of the material. The polymer had a higher molecular weight and was more viscous than the polymer used in Example 3. Example 4 also did not contain any monomer, but did contain a plasticizer.

Upon curing, the material did not produce any tactile heat sensation. The material had good tissue adhesion and was flexible after curing. The material was easily extruded through a 20 gauge bent applicator tip. The material had a blue color due to a small amount of colorant added. A bead of the material did not run when placed on the mixing pad and turned to a vertical position. Table 1 shows the temperature rise value measured, 4.2±0.4° F. This material provided a number of desirable properties.

Example 5

A polymerizable dental barrier material of the present invention containing 93.47% of a high molecular weight aliphatic urethane acrylate polymer having reactive end groups was prepared. Table 2 shows the composition of the material. The reactive polymer used was the same as described in Example 4, however the amount used was increased. Additionally, the material contained a monomer and no plasticizer. The barrier material was thicker than the materials of Examples 3 and 4 due to the viscosity of the reactive polymer selected and the lack of any plasticizer.

Curing upon the finger did not produce a painful heat sensation, however, a slight tingling sensation was detected on occasion. The cured material was more rigid than the material of Example 4, but was still flexible. The material was bent back upon itself without difficulty.

The material was extruded through a 20 gauge bent applicator tip, but due to its viscosity did offer some resistance or back pressure on the plunger when extruded. The amount of back pressure was still within clinically acceptable limits. A bead of the material did not run when placed on the mixing pad and turned to a vertical position. Table 1 shows the temperature rise value measured, 6.1±1.4° F. This material offers some advantages due to its slight rigidity, but still flexible nature combined with greater viscosity.

Example 6

A polymerizable dental barrier material of the present invention containing 76.72% of a high molecular weight aliphatic urethane acrylate polymer having reactive end groups was prepared. Table 2 shows the composition of the material. The reactive polymer used was the same as described in Example 4, however the amount used was slightly decreased. The material contained a monomer, a plasticizer, and a significantly reduced amount of camphorquinone and amine compared to the material of Example 3. Additionally, the material contained a small amount of tri methylol propane tri methacrylate which improved the flow and final toughness of the material. The titanium dioxide provided opacity, the silica provided resistance to flow and FD&C Blue #1 Lake provided blue coloration.

The material was easily dispensed through a 20 gauge applicator tip. A bead of the material did not run when placed on the mixing pad and turned to a vertical position. The material adhered well to a moistened finger or intra-oral tissue. Table 1 shows the temperature rise value measured, 3.7±0.4° F. The material, when cured either on the finger or intra-orally in a continuous manner, caused no heat sensation. After curing, the material was pliable, but tough. The initial and final material was an opaque, light blue color. This appearance provided excellent color contrast to both tooth color and gingival, without any heat sensation or patient discomfort.

TABLE 1

| Material/Example | Laboratory Temperature Rise Test, ° F. |
|---|---|
| Example 1 | 6.4 ± 1.4° F. |
| Example 2 | 6.4 ± 1.5° F. |
| Example 3 | 5.5 ± 0.5° F. |
| Example 4 | 4.2 ± 0.4° F. |
| Example 5 | 6.1 ± 0.4° F. |
| Example 6 | 3.7 ± 0.4° F. |

TABLE 2

| Material/Example | urethane acrylate high mol. wt. polymer | tri methylol propane tri methacrylate | plasticizer | camphorquinone | ethyl 4 di methyl amino benzoate | silica | titanium dioxide | color |
|---|---|---|---|---|---|---|---|---|
| Example 3 | 87.77 | 0.00 | 0.00 | 0.26 | 0.74 | 10.43 | 0.88 | 0.00 |
| Example 4 | 78.09 | 0.00 | 17.00 | 0.09 | 0.23 | 4.23 | 0.34 | 0.02 |
| Example 5 | 93.49 | 1.60 | 0.00 | 0.09 | 0.23 | 4.23 | 0.34 | 0.02 |
| Example 6 | 76.72 | 1.60 | 17.00 | 0.09 | 0.23 | 4.23 | 0.34 | 0.02 |

Various modifications and alterations of this invention will be apparent to those skilled in the art without departing from the scope and spirit of this invention. This invention should not be restricted to that set forth herein for illustrative purposes only.

What is claimed is:

1. A method for forming a polymerizable dental barrier material about dental tissue in the oral cavity of a patient, the method comprising the steps of:

forming at least one high molecular weight polymer with reactive end groups, the at least one high molecular weight polymer having a molecular weight of more than 20,000 g/mol and a concentration ranging from about 50% to about 99% by weight;

adding a polymerization system to the polymer;

disposing the polymer and polymerization system about the patient dental tissue; and causing the polymer to polymerize, whereby polymerization of the polymer produces a minimal exothermic reaction and forms a soft, pliable dental barrier material.

2. A method for forming a polymerizable dental barrier material about dental tissue in the oral cavity of a patient, the method comprising the steps of:

forming at least one high molecular weight polymer with reactive end groups, the at least one high molecular weight polymer having a molecular weight of more than 20,000 g/mol and a concentration ranging from about 50% to about 99% by weight;

adding a monomer having a concentration ranging from greater than 0% to about 10% by weight to the polymer;

adding a polymerization system to the polymer;

disposing the polymer and polymerization system about the patient dental tissue; and causing the polymer to polymerize, whereby polymerization of the polymer produces a minimal exothermic reaction and forms a soft, pliable dental barrier material.

3. The method of claim 1 wherein the heat of polymerization of the dental barrier material is less than 7.9° F.

4. The method of claim 2 wherein the heat of polymerization of the dental barrier material is less than 7.9° F.

5. The method of claim 1 wherein the polymerization system concentration ranges from about 0.15% to about 3.5% by weight.

6. The method of claim 1 wherein the at least one high molecular weight polymer with reactive end groups is silicone, acrylic, urethane, polyether, polysulfide, or a combination thereof.

7. The method of claim 1 wherein the at least one high molecular weight polymer with reactive end groups is a urethane acrylate.

8. The method of claim 1 further comprising the step of: adding a monomer having a concentration ranging from greater than 0% to about 10% by weight.

9. The method of claim 8 wherein the monomer is trimethylol propane trimethacrylate, pentaerythritol trimethacrylate, pentaerythritol tetramethacrylate, dipentaerythritol penta acrylate, or a combination thereof.

10. The method of claim 1 further comprising the step of: adding a filler material having a concentration ranging from greater than 0% to about 50% by weight.

11. The method of claim 10 wherein the filler material is silica, talc, titanium dioxide, bentonite, potassium aluminum silicate, quartz, barium aluminum silicate glass, or any combination thereof.

12. The method of claim 1 wherein the polymerization system includes an initiator, an accelerator, or a combination thereof.

13. The method of claim 12 wherein the initiator is a photoinitiator or an auto cure initiator.

14. The method of claim 13 wherein the auto cure initiator is benzoyl peroxide, cumene hydro peroxide, lauryl peroxide, or a combination thereof.

15. The method of claim 13 wherein the photoinitiator is camphorquinone, diphenyl (2,4,6 trimethylbenzoyl) phosphine oxide, benzyl, benzoin, or a combination thereof.

16. The method of claim 12 wherein the accelerator is an amine, a sulfonate, or a combination thereof.

17. The method of claim 12 wherein the accelerator is N,N di-methyl-p-toluidine, hydroxy ethyl-p-toluidine, ethyl-4-dimethyl amino benzoate, p-toluene sulfinic acid, or a combination thereof.

18. The method of claim 1 further comprising the step of: adding a plasticizer having a concentration ranging from greater than 0% to about 45% by weight.

19. The method of claim 18 wherein the plasticizer is dimethyl phthalate, Bis(2-butoxy ethyl) phthalate, Bis(2-butoxyethyl) adipate, tri(ethylene glycol) bis(2-ethyl hexanoate), tri(ethylene glycol) diacetate, or any combination thereof.

20. The method of claim 6 further comprising the step of: adding an opacifier or a pigment.

21. The method of claim 2 wherein the polymerization system concentration ranges from about 0.15% to about 3.5% by weight.

22. The method of claim 2 wherein the at least one high molecular weight polymer with reactive end groups is silicone, acrylic, urethane, polyether, polysulfide, or a combination thereof.

23. The method of claim 2 wherein the at least one high molecular weight polymer with reactive end groups is a urethane acrylate.

24. The method of claim wherein the monomer is trimethylol propane trimethacrylate, pentaerythritol trimethacrylate, pentaerythritol tetramethacrylate, dipentaerythritol penta acrylate, or a combination thereof.

25. The method of claim 2 further comprising the step of: adding a filler material having a concentration ranging from greater than 0% to about 50% by weight.

26. The method of claim 25 wherein the filler material is silica, talc, titanium dioxide, bentonite, potassium aluminum silicate, quartz, barium aluminum silicate glass, or any combination thereof.

27. The method of claim 2 wherein the polymerization system includes an initiator, an accelerator, or a combination thereof.

28. The method of claim 2 wherein the initiator is a photoinitiator or an auto cure initiator.

29. The method of claim 28 wherein the auto cure initiator is benzoyl peroxide, cumene hydro peroxide, lauryl peroxide, or a combination thereof.

30. The method of claim 28 wherein the photo initiator is camphorquinone, diphenyl (2,4,6 trimethylbenzoyl) phosphine oxide, benzyl, benzoin, or a combination thereof.

31. The method of claim 27 wherein the accelerator is an amine, a sulfonate, or a combination thereof.

32. The method of claim 27 wherein the accelerator is N,N di-methyl-p-toluidine, hydroxy ethyl-p-toluidine, ethyl-4-dimethyl amino benzoate, p-toluene sulfinic acid, or a combination thereof.

33. The method of claim 2 further comprising the step of: adding a plasticizer having a concentration ranging from greater than 0% to about 45% by weight.

34. The method of claim 33 wherein the plasticizer is dimethyl phthalate, Bis(2-butoxy ethyl) phthalate, Bis(2-butoxyethyl) adipate, tri(ethylene glycol) bis(2-ethyl hexanoate), tri(ethylene glycol) diacetate, or any combination thereof.

35. The method of claim 2 further comprising the step of: adding an opacifier or a pigment.

* * * * *